US 12,059,577 B2

(12) United States Patent
Peltola et al.

(10) Patent No.: US 12,059,577 B2
(45) Date of Patent: Aug. 13, 2024

(54) METHOD AND APPARATUS FOR RADIATION TREATMENT PLANNING

(71) Applicant: Siemens Healthineers International AG, Steinhausen (CH)

(72) Inventors: Jarkko Y. Peltola, Tuusula (FI); Mikko Laitinen, Espoo (FI); Heini Hyvönen, Helsinki (FI)

(73) Assignee: Siemens Healthineers International AG, Steinhausen (CH)

( * ) Notice: Subject to any disclaimer, the term of this patent is extended or adjusted under 35 U.S.C. 154(b) by 0 days.

(21) Appl. No.: 17/706,902

(22) Filed: Mar. 29, 2022

(65) Prior Publication Data

US 2023/0310891 A1    Oct. 5, 2023

(51) Int. Cl.
*A61N 5/10* (2006.01)

(52) U.S. Cl.
CPC ......... *A61N 5/1036* (2013.01); *A61N 5/1045* (2013.01); *A61N 5/1075* (2013.01); *A61N 2005/1074* (2013.01)

(58) Field of Classification Search
None
See application file for complete search history.

(56) References Cited

U.S. PATENT DOCUMENTS

2006/0045238 A1* 3/2006 Nguyen ............... A61N 5/103
378/65

2016/0082288 A1* 3/2016 Vahala ................... A61B 5/742
600/411
2016/0144198 A1    5/2016 Löf
2022/0001210 A1* 1/2022 Letourneau ........... A61B 5/055

FOREIGN PATENT DOCUMENTS

EP         3682945 A1    7/2020

OTHER PUBLICATIONS

McNiven, Andrea et al.; A new metric for assessing IMRT modulation complexity and plan deliverability; Med. Phys. 37 (2), Feb. 2010; pp. 505-515.
Younge, Kelly C. et al.; Penalization of aperture complexity in inversely planned volumetric modulated arc therapy; Med. Phys. 39 (11), Nov. 2012; pp. 7160-7170.

(Continued)

*Primary Examiner* — Hoon K Song
(74) *Attorney, Agent, or Firm* — Fitch, Even, Tabin & Flannery LLP

(57) ABSTRACT

A control circuit generates an optimized radiation treatment plan with respect to an adjustable collimation device and then automatically generates at least one quality assurance accuracy value corresponding to the optimized radiation treatment plan. By one approach, the aforementioned plan comprises a plurality of treatment fields. In such a case, automatically generating at least one quality assurance accuracy value can comprise, at least in part, automatically generating at least one quality assurance accuracy value for each of at least a substantial number (or all) of those treatment fields. By one approach, the aforementioned quality assurance accuracy value comprises a dimensionless metric. This dimensionless metric may represent, for example, dosimetric accuracy corresponding to the optimized radiation treatment plan.

18 Claims, 6 Drawing Sheets

(56) References Cited

OTHER PUBLICATIONS

McGarry, Conor K. et al.; The role of complexity metrics in a multi-institutional dosimetry audit of VMAT; Br J Radiol 2016; 89:20150445; 7 pages.
Younge, Kelly C. et al.; Predicting deliverability of volumetric-modulated arc therapy (VMAT) plans using aperture complexity analysis; Journal of Applied Clinical Medical Physics, vol. 17, No. 4; 2016; pp. 124-131.
Glenn, Mallory C. et al.; Treatment plan complexity does not predict IROC Houston anthropomorphic head and neck phantom performance; Phys. Med. Biol. 63 (2018) 205015; 10 pages.
Hernandez, Victor et al.; Comparison of complexity metrics for multi-institutional evaluations of treatment plans in radiotherapy; Physics and Imaging in Radiation Oncology 5 (2018) 37-43.
Santos, Tania et al.; Evaluation of the complexity of treatment plans from a national IMRT/VMAT audit—Towards a plan complexity score; Physica Medica 70 (2020) 75-84.
International Search Report and Written Opinion from Application No. PCT/EP2023/057435 dated Jun. 16, 2023; 16 pages.
Klein, Eric E. et al.; Task Group 142 report: Quality assurance of medical accelerators; Med. Phys. 36 (9) Sep. 2009; pp. 4197-4212.

\* cited by examiner

METHOD AND APPARATUS FOR RADIATION TREATMENT PLANNING

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

When generating radiation treatment plans, it can be useful to know that the dose calculations agree (or likely agree) with actual measurements. Unfortunately, small multi-leaf collimator apertures specified by a given plan can result in modeling error. That, in turn, can lead to the plan quality assurance (QA) not passing a required tolerance criteria.

BRIEF DESCRIPTION OF THE DRAWINGS

The above needs are at least partially met through provision of the method and apparatus for radiation treatment planning described in the following detailed description, particularly when studied in conjunction with the drawings, wherein.

Figure 1:
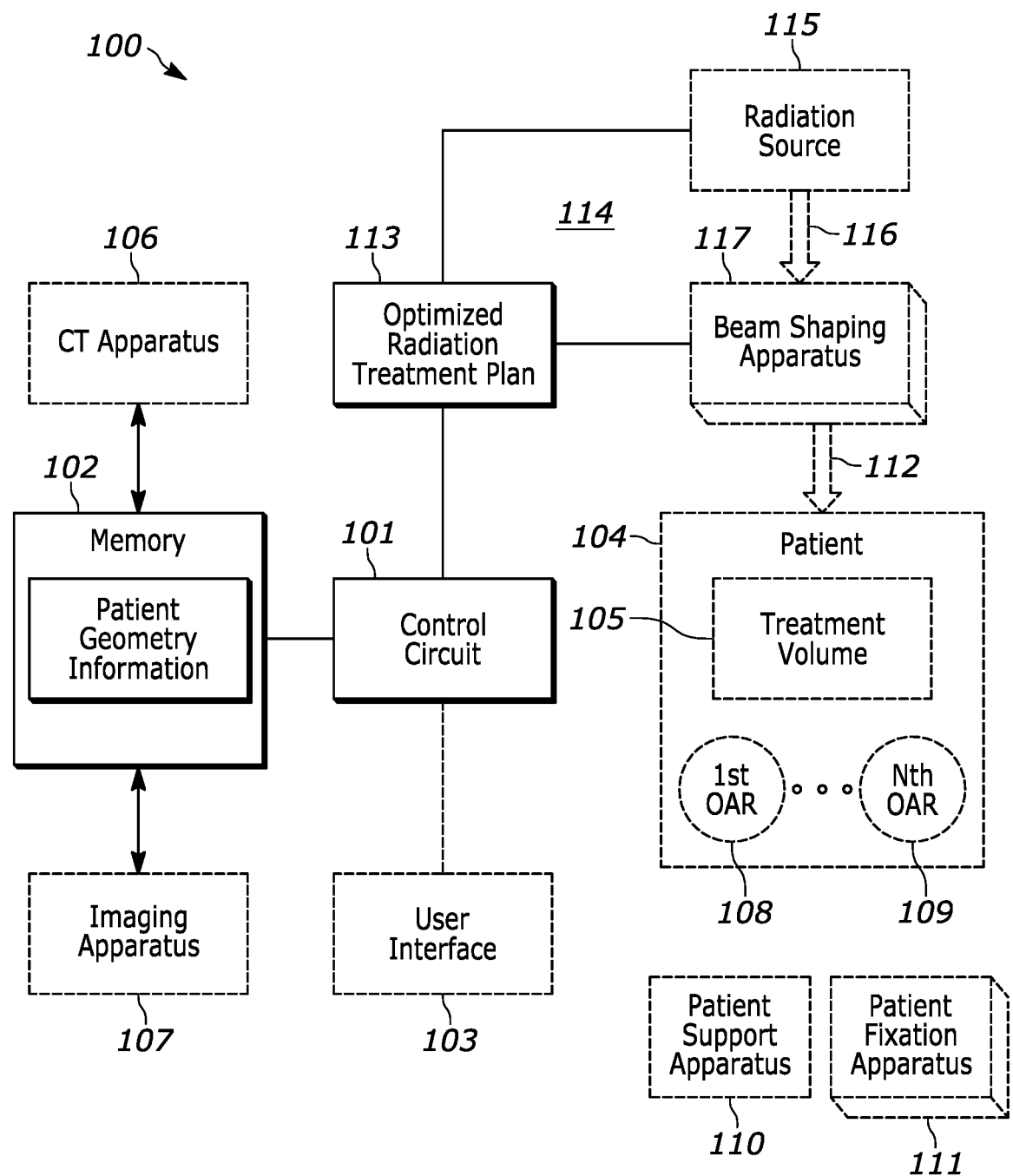
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments a control circuit generates an optimized radiation treatment plan with respect to an adjustable collimation device and then automatically generates at least one quality assurance accuracy value corresponding to the optimized radiation treatment plan. By one approach, the aforementioned plan comprises a plurality of treatment fields. In such a case, automatically generating at least one quality assurance accuracy value can comprise, at least in part, automatically generating at least one quality assurance accuracy value for each of at least a substantial number (or all) of those treatment fields.

By one approach, the aforementioned quality assurance accuracy value comprises a dimensionless metric. This dimensionless metric may represent, for example, dosimetric accuracy corresponding to the optimized radiation treatment plan.

By one approach, the foregoing may include calculating the dimensionless metric by evaluating movable-edge penumbra ratios corresponding to the adjustable collimation apparatus. (When the adjustable collimation apparatus comprises a multi-leaf collimator, for example, the aforementioned movable-edge may comprise a leaf edge.) The foregoing calculation may further comprise, for example, calculating a term that at least approximates a total penumbra area for a given control point for a given one of the treatment fields (for example, by calculating what portion of an adjustable collimation apparatus aperture that corresponds to the given control point is within a predetermined penumbra distance from corresponding movable edges.

These teachings will accommodate, for example, presenting information regarding the aforementioned quality assurance accuracy value via a user interface. By one approach, these teachings will further accommodate receiving input from a user via that user interface in response to presenting that information, modifying the radiation treatment plan as a function of that input, re-optimizing the radiation treatment plan as a function of that input, and administering therapeutic radiation to a patient using the re-optimized radiation treatment plan.

So configured, these teachings provide a metric that can serve as a QA accuracy value and that can be presented for each treatment field. More particularly, this metric can serve as, for example, a multi-leaf collimator complexity metric that evaluates dosimetric accuracy of a given radiation treatment plan. Generally speaking, planning can occur more quickly than conducting QA measurements. By providing a useful metric that represents estimated potential modeling errors that correspond to a given plan, a user can, for example, choose from amongst different candidate plans as a function, at least in part, of the aforementioned metric to thereby help select a plan more likely to pass the QA evaluation.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular radiation treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
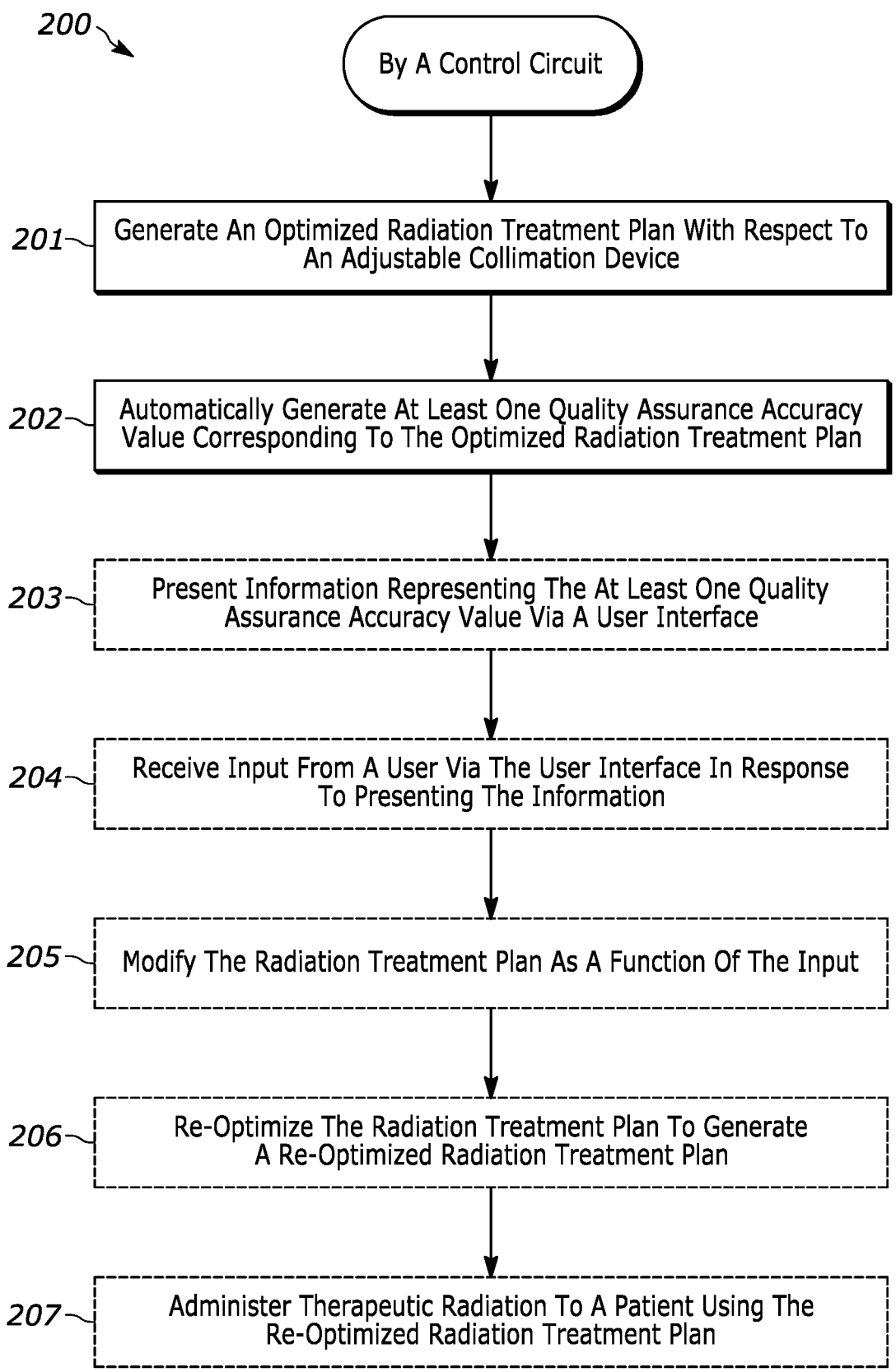
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 serves to facilitate generating an optimized radiation treatment plan 113 to thereby facilitate treating a particular patient with therapeutic radiation using a particular radiation treatment platform per that optimized radiation treatment plan.

At block 201, this process 200 provides for generating an optimized radiation treatment plan with respect to an adjustable collimation device. This example presumes that this plan corresponds to a given patient. There are various approaches to optimizing a radiation treatment plan known in the art. As these teachings are not overly sensitive to any particular selection in these regards, further elaboration regarding such practices is not provided here for the sake of brevity.

Various adjustable collimation devices are known in the art, and include adjustable jaws and multi-leaf collimators. For the sake of an illustrative example, the following description presumes that the adjustable collimation device comprises a multi-leaf collimator. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and which can selectively move towards and away from one another. A typical multi-leaf collimator has many such pairs of leaves, often upwards of twenty, fifty, or even one hundred such pairs.

At block 202, this process 200 then provides for automatically generating at least one quality assurance accuracy value that corresponds to the optimized radiation treatment plan.

In many application settings the optimized radiation treatment plan itself will comprise a plurality of treatment fields. Each treatment field can comprise exposing the patient's treatment volume from a corresponding angle to a radiation beam that is at least partially shaped and modulated by a given aperture (or apertures) formed by the multi-leaf collimator. In such a case, these teachings can provide for automatically generating a quality assurance accuracy value that directly corresponds to each of at least a substantial number of the treatment fields (such as at least a majority of the treatment fields, at least ninety percent of the treatment fields, or even all of the treatment fields).

By one approach, the aforementioned quality assurance accuracy value can comprise a dimensionless metric that represents dosimetric accuracy corresponding to the optimized radiation treatment plan. Such a metric can serve, for example, during quality assurance (QA) testing of a radiation treatment platform. QA comprises a known area of prior art endeavor. See, for example, American Association of Physical Medicine (AAPM), Task Group 142 (TG-142), report entitled "Quality Assurance of Medical Accelerators," 2009, which is hereby incorporated herein by this reference.

By one approach, automatic generation of this metric can comprise, at least in part, calculating the dimensionless metric by evaluating movable-edge (such as leaf edges) penumbra ratios corresponding to the adjustable collimation apparatus (in this example, the multi-leaf collimator).

Figure 3:
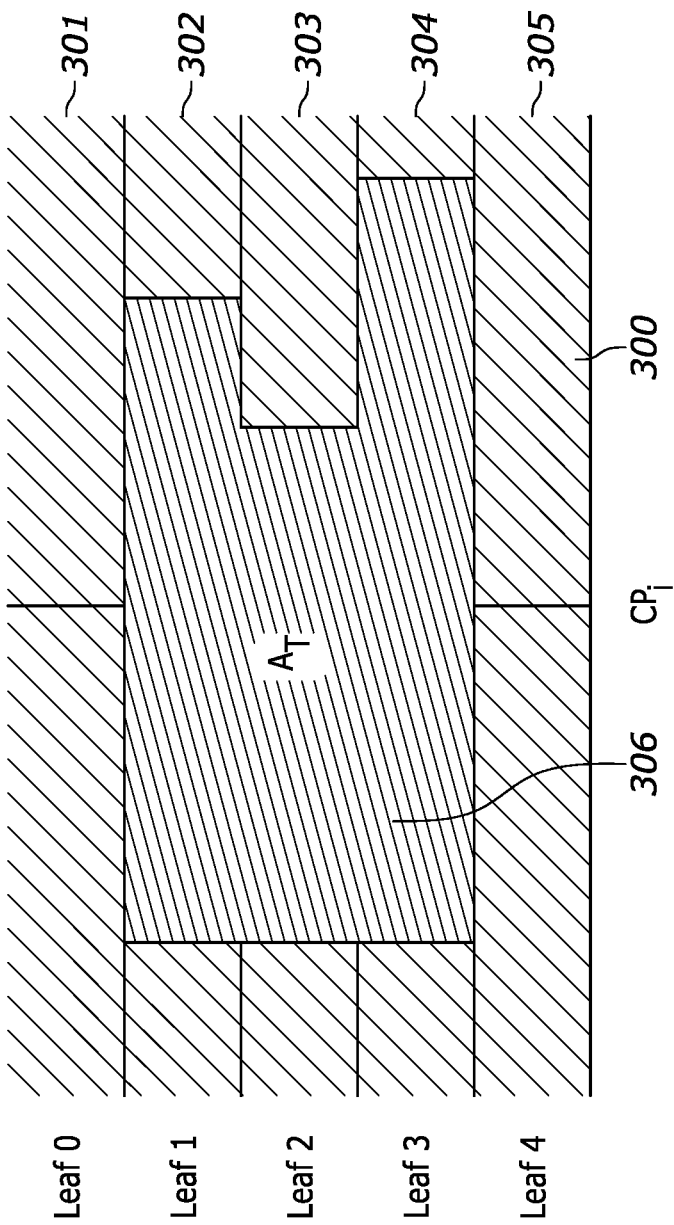
FIG. 3 comprises a side-elevational view as configured in accordance with various embodiments of these teachings.
Figure 4:
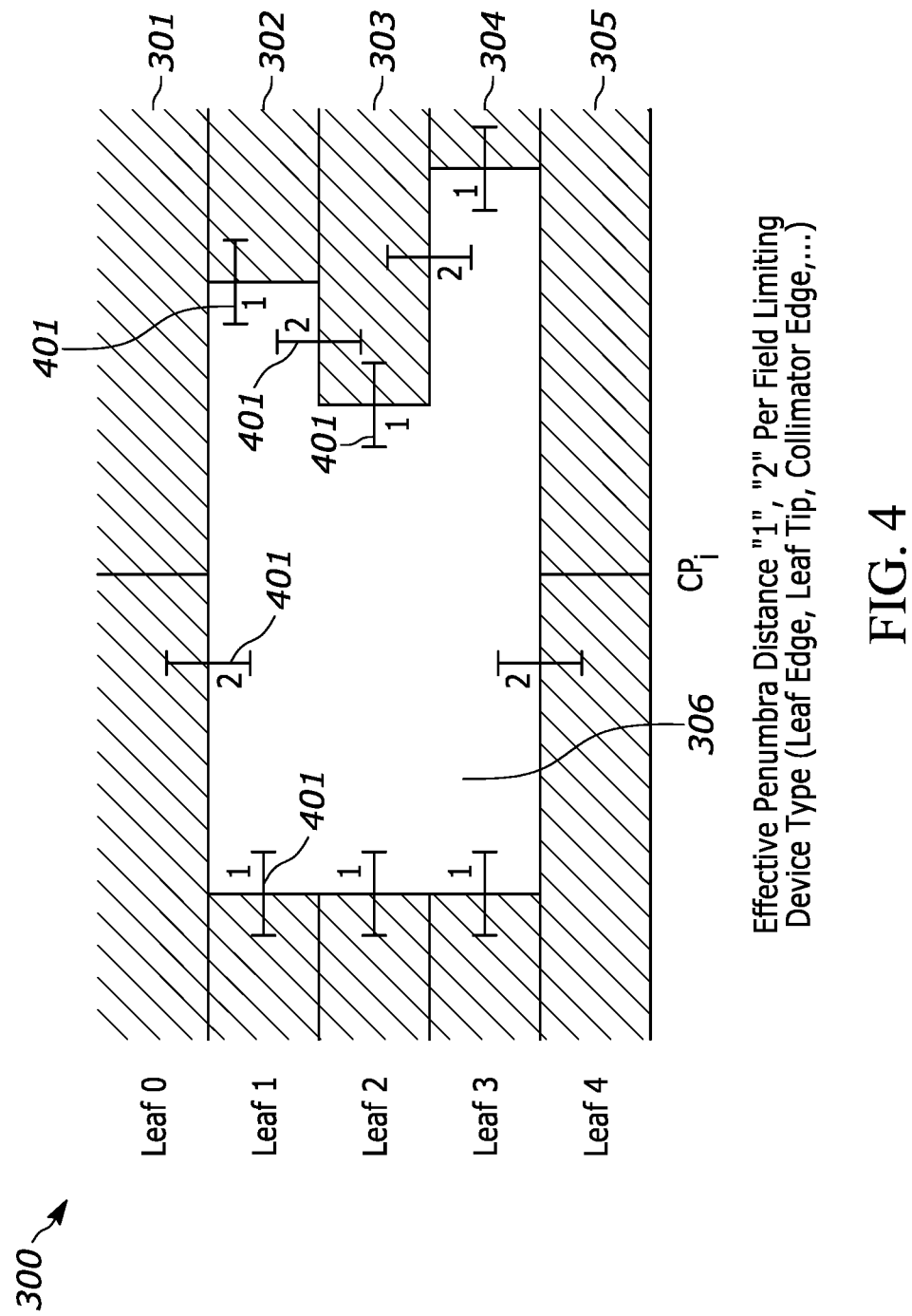
FIG. 4 comprises a side-elevational view as configured in accordance with various embodiments of these teachings.
Figure 5:
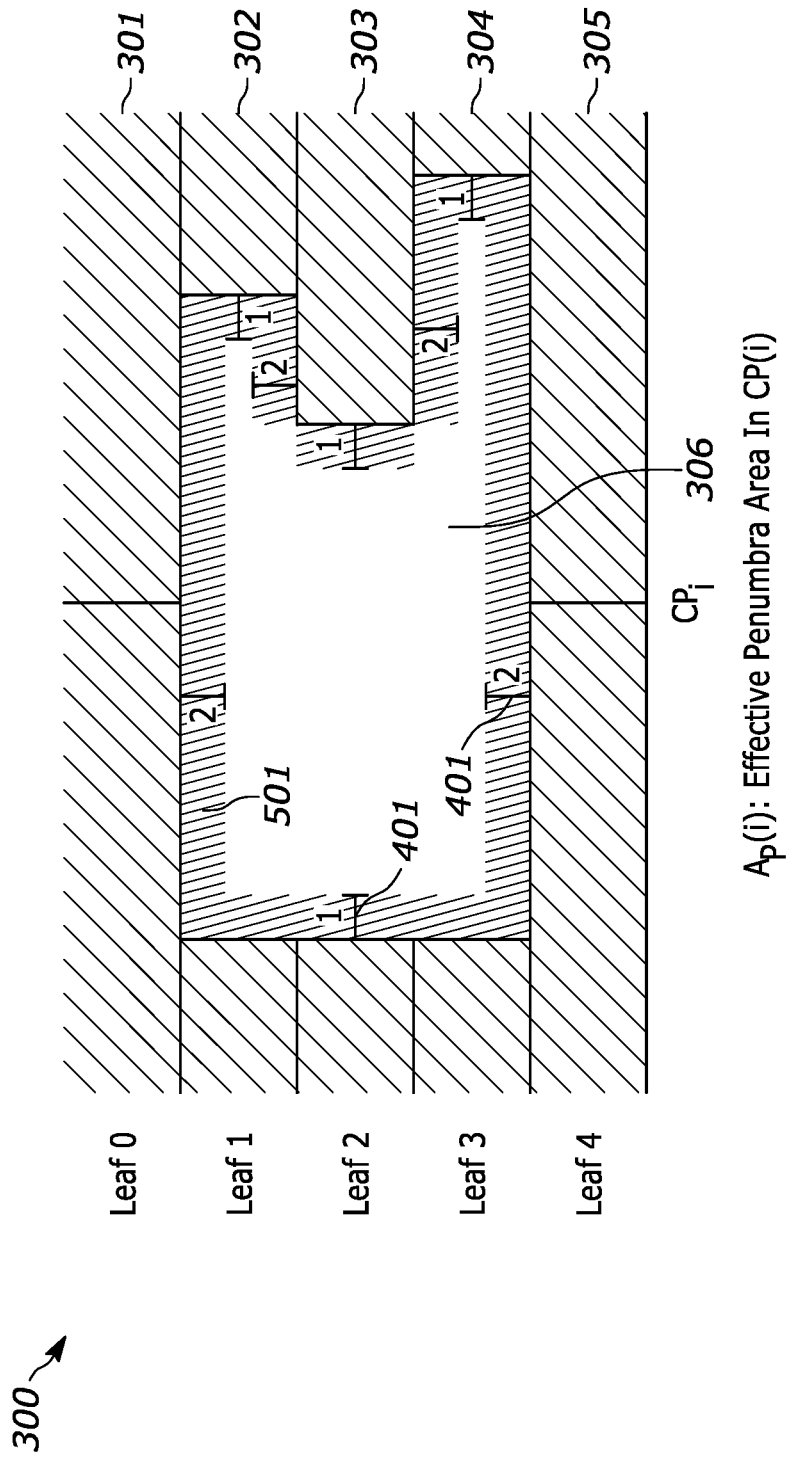
FIG. 5 comprises a side-elevational view as configured in accordance with various embodiments of these teachings.

FIGS. 3-5 present a simple illustrative example in these regards. FIG. 3 presents a multi-leaf collimator 300 having five leaf pairs (leaf pair 0 denoted by reference numeral 301, leaf pair 1 denoted by reference numeral 302, leaf pair 2 denoted by reference numeral 303, leaf pair 3 denoted by reference numeral 304, and leaf pair 4 denoted by reference numeral 305). These leaves are positioned at this particular control point CP, to form an aperture 306 having a total field opening area (or total aperture area) AT(i). FIG. 4 illustrates the effective penumbra distances (some of which are denoted by reference numeral 401) that correspond to the edges of the leaves that form the aperture (including both side edges and tip edges thereof). And FIG. 5 illustrates the effective penumbra area AP(i) 501 at this control point within the aperture 306.

The foregoing can comprise, by way of example, calculating a term that at least approximates a total penumbra area for a given control point for a given one of the treatment fields. (The degree of approximation can vary as desired with the needs and/or requirements of the application setting. For example, the degree of approximation may be within twenty percent, fifteen percent, ten percent, five percent, one percent, or some other degree of choice.) The latter, in turn, can comprise calculating what portion of an adjustable collimation apparatus (such as the multi-leaf collimator in this example) aperture that corresponds to the given control point is within a predetermined penumbra distance from corresponding movable edges (such as multi-leaf collimator leaf edges).

At optional block 203, if desired, this process 200 will accommodate presenting information representing the aforementioned at least one quality assurance accuracy value via a user interface 103 as described above. This may comprise, for example, presenting total penumbra ratio values for the treatment plan and for each field separately.

At optional block 204, this process 200 provides for receiving input from a user via that user interface 103 in response to presenting such information. This may comprise, for example, receiving user input comprising new values that can be used to re-optimize the plan. With momentary reference to FIG. 6, and by way of example, this could comprise the user providing input specifying that the maximum penumbra ratio must be less than ninety-one percent.

By another approach, the user input may include a command to at least attempt to lower the current penumbra ratio values automatically. In such a case, the optimization algorithm can be configured to automatically generate an objective that works to push the achieved penumbra ratio values down by attaching a standard squared cost-function term to them.

By yet another approach, the user input may comprise a maximum limit for the penumbra ratio values (since the larger the penumbra ratio, the higher the risk of failing at plan QA). Such a limit may apply per field (in which case, there could be one limit that applies to all fields or there may be individual limits that each apply to only one field or to a subset of the fields) and/or per plan. In some application settings it may be helpful to know what the minimum value that can be achieved. With the foregoing in mind, the total penumbra area can also be normalized so that the value 0 refers to a plan that is totally conformal (where target projections are followed by the collimation devices and no leaf modulation is done, this representing the best plan that can be achieved from a QA perspective). This would then mean that any non-zero penumbra ratio value can be considered as increasing the complexity and therefore increasing the risk of failing QA. This would also mean that any plan can be re-optimized so that user can ask for any specified penumbra ratio value [for example, within the range of 0 . . . 1].

At optional block 205, the process 200 provides for modifying the radiation treatment plan as a function of that received user input and then, at block 206, re-optimizing the radiation treatment plan to generate a re-optimized radiation treatment plan.

At optional block 207, that re-optimized radiation treatment plan can be used to administer therapeutic radiation to a patient via, for example, the aforementioned radiation treatment platform 114.

Additional details will now be provided in conjunction with an illustrative example. It shall be understood that the specific details of this example are intended to serve an illustrative purpose and should not be taken as examples of limitations with respect to the practice of these teachings.

As noted earlier, a radiation treatment plan typically comprises a set of fields that each consist of a sequence of control points that each define the treatment machine's axis, multi-leaf collimator leaf positions, collimation positions, and the level of administered radiation. In this example, the irradiation opening area that corresponds to the leaf positions is calculated for each control point. This area can be limited by leaf-tip positions, or can also include leaf sides as desired. (Collimation jaws edges can also be included if present.)

A term that approximates the total penumbra area, AP, is calculated by determining how much of the aforementioned opening is within a penumbra distance from the leaf tips/sides. While the term "penumbra" usually refers to a specific mathematical term that describes the scattering of the radiation under the leaf edges, in this example, the penumbra distance represents the usual penumbra combined with an approximation of errors associated with leaf positioning. Typical resultant distances in an ordinary application setting are only a very few millimeters, such as 2.8 mm for a leaf tip and 2.3 mm for a leaf side.

A penumbra ratio (PR) for a given control point (i) can be calculated as $$PR(i)=(AP(i))/(AT(i)).$$

If desired, a normalization approach can be used to represent the PR(i) value in the scale of [0,1], such that 0 refers to a Penumbra Area (Ap) that is the minimum that can be achieved in control point i. If A_c is that minimum value (all leaves/collimation devices set to boundary of the target projection at cp i), then normalized PR(i) can be calculated as:

$$PRnorm(i) = \frac{(A_p(i) - A_c(i))}{A\_t(i) - A_c(i)}.$$

This normalized PR can be inserted in the previous equation instead of PR, and then one would obtain a normalized PR for whole field.

The actual penumbra metric for a given field is then summed over some (or, more typically, all) of the control points in that field. In this example, the foregoing can be weighted by the ratio of the monitor units (MU) that are delivered through each control point. (Monitor units are a known measure of machine output from a clinical accelerator for radiation therapy.) In this example, the weight for a control point (i) is can be calculated as $$w(i)=0.5*(CMW(i)-CMW(i-1))+0.5*(CMW(+1)-CMW(i))$$

where CMW refers to the cumulative meterset weight (wherein the latter refers to a dimensionless cumulative measure from 0 to 1 over the sequence of control points in a treatment field, and which indicates much radiation needs to be applied between control points).

A dimensionless (i.e., unit-less) complexity metric for this field having these control points can then be calculated as $$P(\text{field}) = \left(\frac{1}{\sum_{i=1}^{N} w(i)}\right) * \sum_{i=1}^{N} (PR(i)*w(i))$$

Both sums go over control points (i) from 1 to N. By one approach the penumbra distances can be a function of the angle of incidence between the incoming radiation and the leaf tips/sides. A different penumbra can be used when a collimation jaw defines the opening as versus a collimator leaf. A different weighting between the penumbra areas caused by different mechanical beam limiting devices can be employed as appropriate and as desired.

As the aperture gets smaller, the total aperture area may become smaller than the penumbra area. Such a situation can result in a quality assurance accuracy value that is larger than "1." If desired, these teachings can be configured to cap the value at "1." Or, if desired, the actual greater-than-"1" result may be provided as the value.

Figure 6:
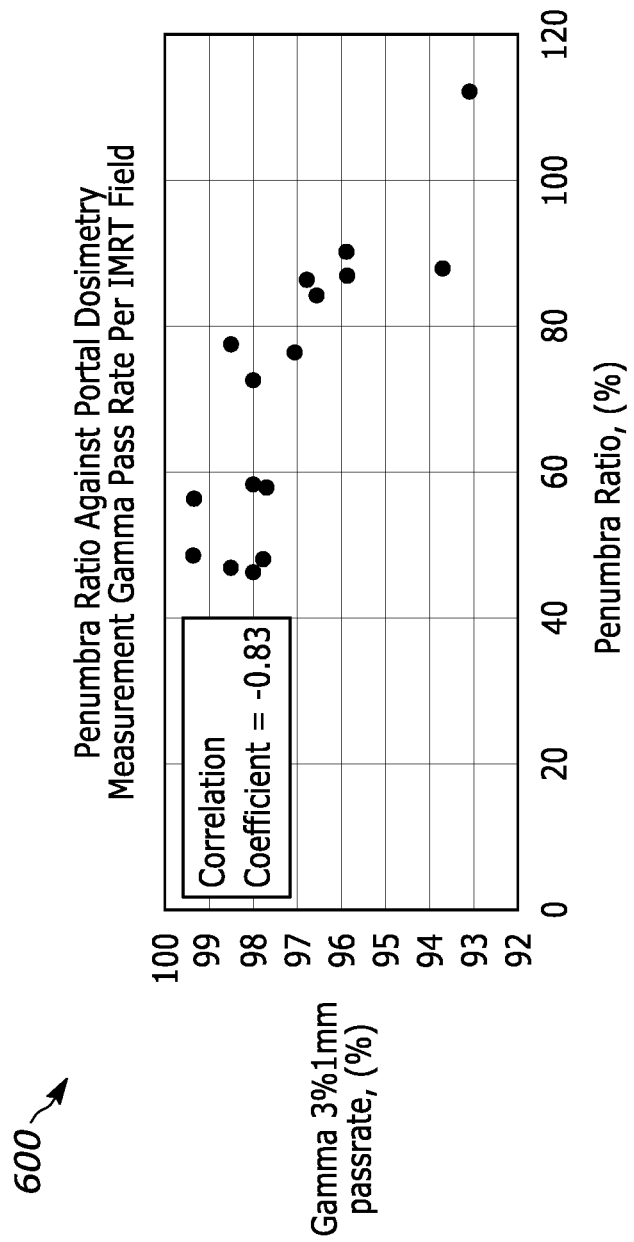
FIG. 6 comprises a graph as configured in accordance with various embodiments of these teachings.

FIG. 6 presents a graph 600 representing penumbra ratios against portal dosimetry gamma pass rates for separate intensity-modulated radiation therapy (IMRT) fields. Effective penumbra ratios used to calculate penumbra ratios in this example were px=2.8 mm and py=2.3 mm. Gamma criteria was 3% and 1 mm and threshold was 80%. This graph illustrates that increasing the penumbra ratio in a plan produces a worse Gamma pass rate between calculated and measured doses, and that after a certain ratio value, the pass rate becomes undesirable. This separating value can be used to evaluate plans and to signal the user when a plan should be re-evaluated/re-optimized. Furthermore, the correlation coefficient between two variables may be considered strong when its absolute value is larger than 0.7. With these two variables in FIG. 6 the correlation is −0.83 which indicates a strong correlation between penumbra ratio and dosimetric accuracy.

Compared against other prior art multi-leaf collimator complexity metrics, the applicant has determined that the present teachings tend to provide a better correlation to measured comparisons. Those skilled in the art will appreciate that these teachings yield a dimensionless metric reflecting multi-leaf collimator complexity that avoids requiring special equipment or that require undue treatment machine and clinician time. The resultant metric can provide a simple way of pre-ranking radiation treatment plans and to help the clinician decide whether to accept a given generated radiation treatment plan or to work to further better the result.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method comprising:
by a control circuit:
generating an optimized x-ray radiation treatment plan with respect to an adjustable collimation device, wherein the optimized x-ray radiation treatment plan comprises a plurality of treatment fields;
automatically generating at least one quality assurance accuracy value corresponding to the optimized x-ray radiation treatment plan by, at least in part, automatically generating at least one quality assurance accuracy value for each of at least a substantial number of the treatment fields.

2. The method of claim 1 wherein automatically generating at least one quality assurance accuracy value for each of at least a substantial number of the treatment fields comprises automatically generating at least one quality assurance accuracy value for each of the treatment fields.

3. The method of claim 1 wherein the quality assurance accuracy value comprises a dimensionless metric.

4. The method of claim 3 wherein the dimensionless metric represents dosimetric accuracy corresponding to the optimized x-ray radiation treatment plan.

5. The method of claim 4 wherein automatically generating the at least one quality assurance accuracy value corresponding to the optimized x-ray radiation treatment plan comprises, at least in part, calculating the dimensionless metric by evaluating movable-edge penumbra ratios corresponding to the adjustable collimation apparatus.

6. The method of claim 5 wherein calculating the dimensionless metric by evaluating movable-edge penumbra ratios corresponding to the adjustable collimation apparatus comprises, at least in part, calculating a term that at least approximates a total penumbra area for a given control point for a given one of the treatment fields.

7. The method of claim 6 wherein calculating the term that at least approximates the total penumbra area for a given control point for a given one of the treatment fields comprises, at least in part, calculating what portion of an adjustable collimation apparatus aperture that corresponds to the given control point is within a predetermined penumbra distance from corresponding movable edges.

8. The method of claim 1 further comprising:
presenting information representing the at least one quality assurance accuracy value via a user interface.

9. The method of claim 8 further comprising:
receiving input from a user via the user interface in response to presenting the information;
modifying the x-ray radiation treatment plan as a function of the input;
re-optimizing the x-ray radiation treatment plan to generate a re-optimized x-ray radiation treatment plan;
administering therapeutic radiation to a patient using the re-optimized x-ray radiation treatment plan.

10. An apparatus comprising:
a control circuit configured to:
generate an optimized x-ray radiation treatment plan with respect to an adjustable collimation apparatus, wherein the optimized x-ray radiation treatment plan comprises a plurality of treatment fields;
automatically generate at least one quality assurance accuracy value corresponding to the optimized x-ray radiation treatment plan by, at least in part, automatically generating at least one quality assurance accuracy value for each of at least a substantial number of the treatment fields.

11. The apparatus of claim 10 wherein the control circuit is configured to automatically generate at least one quality assurance accuracy value for each of at least a substantial number of the treatment fields by automatically generating at least one quality assurance accuracy value for each of the treatment fields.

12. The apparatus of claim 10 wherein the quality assurance accuracy value comprises a dimensionless metric.

13. The apparatus of claim 12 wherein the dimensionless metric represents dosimetric accuracy corresponding to the optimized x-ray radiation treatment plan.

14. The apparatus of claim 13 wherein the control circuit is configured to automatically generate the at least one quality assurance accuracy value corresponding to the optimized radiation treatment plan by, at least in part, calculating the dimensionless metric by evaluating movable-edge penumbra ratios corresponding to the adjustable collimation apparatus.

15. The apparatus of claim 14 wherein the control circuit is configured to calculate the dimensionless metric by evaluating movable-edge penumbra ratios corresponding to the adjustable collimation apparatus by, at least in part, calculating a term that at least approximates a total penumbra area for a given control point for a given one of the treatment fields.

16. The apparatus of claim 15 wherein the control circuit is configured to calculate the term that at least approximates the total penumbra area for a given control point for a given one of the treatment fields by, at least in part, calculating what portion of an adjustable collimation apparatus aperture that corresponds to the given control point is within a predetermined penumbra distance from corresponding movable edges.

17. The apparatus of claim 10 wherein the control circuit is further configured to:
present information representing the at least one quality assurance accuracy value via a user interface.

18. The apparatus of claim 17 wherein the control circuit is further configured to:
receive input from a user via the user interface in response to presenting the information;
modify the radiation treatment plan as a function of the input;
re-optimize the x-ray radiation treatment plan to generate a re-optimized x-ray radiation treatment plan;
facilitate administering therapeutic radiation to a patient using the re-optimized x-ray radiation treatment plan.

* * * * *